(12) United States Patent
Jimenez et al.

(10) Patent No.: US 7,793,375 B2
(45) Date of Patent: Sep. 14, 2010

(54) POWERED TOOTHBRUSH WITH CURVED NECK AND FLEXIBLE SHAFT

(75) Inventors: Eduardo Jimenez, Manalapan, NJ (US); Fung Kut Hui, Hong Kong (CN); John J. Gatzemeyer, Hillsborough, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 10/436,218

(22) Filed: May 12, 2003

(65) Prior Publication Data
US 2004/0226119 A1 Nov. 18, 2004

(51) Int. Cl.
*A61C 17/26* (2006.01)
(52) U.S. Cl. .......................... 15/22.1; 15/22.4
(58) Field of Classification Search ................... 15/22.1, 15/22.2, 22.4, 28, 23
See application file for complete search history.

(56) References Cited

U.S. PATENT DOCUMENTS

| | | | |
|---|---|---|---|
| 2,129,002 A | 9/1938 | Gold | |
| 2,562,805 A * | 7/1951 | Martinez | 15/23 |
| 2,916,752 A * | 12/1959 | Baker | 15/28 |
| 3,699,952 A | 10/1972 | Waters et al. | |
| 3,757,419 A | 9/1973 | Hopkins | |
| 3,822,432 A * | 7/1974 | Skinner | 15/23 |
| D237,187 S | 10/1975 | Fattaleh | |
| 4,060,870 A | 12/1977 | Cannarella | |
| 4,250,587 A * | 2/1981 | Beck, Jr. | 15/28 |
| 4,274,173 A | 6/1981 | Cohen | |
| 4,420,851 A | 12/1983 | Wiener | |
| D278,764 S | 5/1985 | Olsen | |
| 4,603,448 A * | 8/1986 | Middleton et al. | 15/22.1 |
| D294,885 S | 3/1988 | Mollenhoff | |
| D321,285 S | 11/1991 | Hirabayashi | |
| 5,088,145 A | 2/1992 | Whitefield | |
| 5,099,536 A * | 3/1992 | Hirabayashi | 15/28 |
| 5,170,525 A * | 12/1992 | Cafaro | 15/28 |
| 5,173,983 A * | 12/1992 | Le | 15/28 |
| D334,842 S | 4/1993 | Lemon et al. | |
| 5,247,716 A * | 9/1993 | Bock | 15/22.1 |
| 5,276,932 A | 1/1994 | Byrd | |
| 5,311,633 A | 5/1994 | Herzog et al. | |
| 5,353,460 A * | 10/1994 | Bauman | 15/22.1 |
| 5,504,961 A | 4/1996 | Yang | |
| 5,625,916 A * | 5/1997 | McDougall | 15/28 |
| 5,864,911 A * | 2/1999 | Arnoux et al. | 15/23 |
| 6,000,083 A * | 12/1999 | Blaustein et al. | 15/28 |

(Continued)

FOREIGN PATENT DOCUMENTS

CN 2238625 9/1996

(Continued)

OTHER PUBLICATIONS

Search Report for Taiwan Patent Application No. 93113119.

*Primary Examiner*—Laura C. Guidotti
(74) *Attorney, Agent, or Firm*—Amy M. Fernandez

(57) ABSTRACT

A powered toothbrush having a curved neck and a flexible shaft within said neck is provided. In a preferred embodiment, a powered toothbrush having a curved neck of a constant radius, a flexible shaft and a clutch mechanism to disengage the flexible shaft from a drive mechanism upon overload is provided.

20 Claims, 2 Drawing Sheets

U.S. PATENT DOCUMENTS

| | | |
|---|---|---|
| 6,138,310 A | 10/2000 | Porper et al. |
| 6,230,717 B1 | 5/2001 | Marx et al. |
| 6,446,294 B1 * | 9/2002 | Specht ................. 15/22.1 |
| 6,795,993 B2 * | 9/2004 | Lin ........................ 15/28 |
| 2002/0039720 A1 | 4/2002 | Marx et al. |
| 2002/0124333 A1 | 9/2002 | Hafliger et al. |
| 2002/0138928 A1 * | 10/2002 | Calabrese ............. 15/22.1 |
| 2003/0000031 A1 | 1/2003 | Zhuan |
| 2003/0079304 A1 * | 5/2003 | Dworzan ............... 15/22.1 |

FOREIGN PATENT DOCUMENTS

| | | |
|---|---|---|
| CN | 2238625 | 10/1996 |
| CN | 2416868 | 1/2001 |
| DE | 3301865 | 7/1984 |
| DE | 100 29 674 A | 1/2002 |
| GB | 477 799 A | 1/1938 |
| GB | 2366995 A | 3/2002 |

* cited by examiner

POWERED TOOTHBRUSH WITH CURVED NECK AND FLEXIBLE SHAFT

BACKGROUND OF THE INVENTION

1. Field of the Invention

The present invention relates to powered toothbrushes, and more particularly, to a powered toothbrush having a curved neck of a constant curvature and a curved flexible shaft.

2. Discussion of Related Art

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of the toothbrush by a user, provide superior cleaning than manual toothbrushes. Typically, powered toothbrushes are powered by disposable or rechargeable batteries that power an electric motor that in turn drives a toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw bones, and each row of teeth consequently has a convex outer curve and a concave inner curve. Individual teeth often have extremely complex surfaces, with areas that may be flat, concave or convex. The more precise the contact between the bristles and the tooth surface, the more effective the toothbrush may be in cleaning, whitening and/or stimulating.

Although powered toothbrushes such as those described immediately above provide advantages over manual toothbrushes, they are not designed for engaging teeth in hard to reach areas of the mouth. Further, the shafts of such powered toothbrushes are not designed to allow for efficient contact between the bristles and the tooth surface. Additionally, such powered toothbrushes utilize multiple, segmented drive shafts coupled to gears, which complicate the powered toothbrush and increase the failure rate.

OBJECTS OF THE INVENTION

Therefore, it is an object of the invention to provide a powered toothbrush which avoids the aforementioned deficiencies of the prior art.

It is also an object of this invention to provide a powered toothbrush with improved ergonomic design.

It is another object of this invention to provide a powered toothbrush with a curved neck of a constant curvature and a single flexible shaft.

It is a further object of this invention to provide a powered toothbrush wherein the single flexible shaft is not engaged to gears.

It is still another object of this invention to provide a powered toothbrush with a clutch mechanism.

Various other objects, advantages and features of the present invention will become readily apparent from the ensuing detailed description and the novel features will be particularly pointed out in the appended claims.

SUMMARY OF THE INVENTION

This invention relates to a powered toothbrush which has been designed to clean teeth in hard to reach areas of the mouth. The powered toothbrush of this invention includes a handle portion having a base member at one end thereof. A curved neck portion extends from the other end of the handle portion with a head coupled to the neck. The head includes at least one bristle carrier connected to a flexible drive shaft for moving the at least one carrier in a first rotatable direction. In a preferred embodiment, the powered toothbrush includes two bristle carriers.

In accordance with one embodiment of the present invention, a powered toothbrush is provided having a handle having an inner cavity formed therein and a base member at one end thereof; a rotary drive member disposed within said inner cavity; a curved tubular neck portion extending from the other end of said handle portion with a head coupled to the neck portion, the head including at least one bristle carrier having bristles, wherein the at least one said bristle carriers is adapted to move in a first rotational direction; and a flexible drive shaft for moving the at least one bristle carrier in a first rotational direction, having a first end and a second end, rotatably disposed within said curved tubular neck portion, the first end thereof being drivably connected to said drive member and the second end thereof extending through the outer end of said curved tubular neck portion, said flexible drive shaft being rotationally responsive to said rotary drive member.

In accordance with another embodiment of the present invention, a powered toothbrush is provided having a handle having an inner cavity formed therein and a base member at one end thereof; a rotary drive member disposed within said inner cavity; a curved tubular neck portion having a constant radius extending from the other end of said handle portion with a head coupled to the neck portion, the head including at least one bristle carrier having bristles, wherein the at least one bristle carrier is adapted to move in a first rotational direction; and a flexible drive shaft for moving the at least one bristle carrier in a first rotational direction, having a first end and a second end, rotatably disposed within said curved tubular neck portion, the first end thereof being drivably connected to said drive member and the second end thereof extending through the outer end of said curved tubular neck portion, said flexible drive shaft being rotationally responsive to said rotary drive member.

In accordance with yet another embodiment of the present invention, a powered toothbrush is provided including a handle having an inner cavity formed therein and a base member at one end thereof; a rotary drive member disposed within said inner cavity, said drive member comprising a clutch mechanism; a curved tubular neck portion extending from the other end of said handle portion with a head coupled to the neck portion, the head including at least one bristle carrier having bristles, wherein the at least one of the bristle carriers is to move in a first rotational direction; and a flexible drive shaft for moving the at least one bristle carrier in a first rotational direction, having a first end and a second end, rotatably disposed within said curved tubular neck portion, the first end thereof being drivably connected to said drive member and the second end thereof extending through the outer end of said curved tubular neck portion, said flexible drive shaft being rotationally responsive to said rotary drive member; wherein said clutch mechanism disengages said flexible drive shaft upon an overpressure to prevent damage to said bristles.

BRIEF DESCRIPTION OF THE DRAWINGS

The following detailed description given by way of example, but not intended to limit the invention solely to the specific embodiments described, may best be understood in connection with the accompanying drawings in which.

DETAILED DESCRIPTION OF CERTAIN PREFERRED EMBODIMENTS OF THE PRESENT INVENTION

Figure 1:
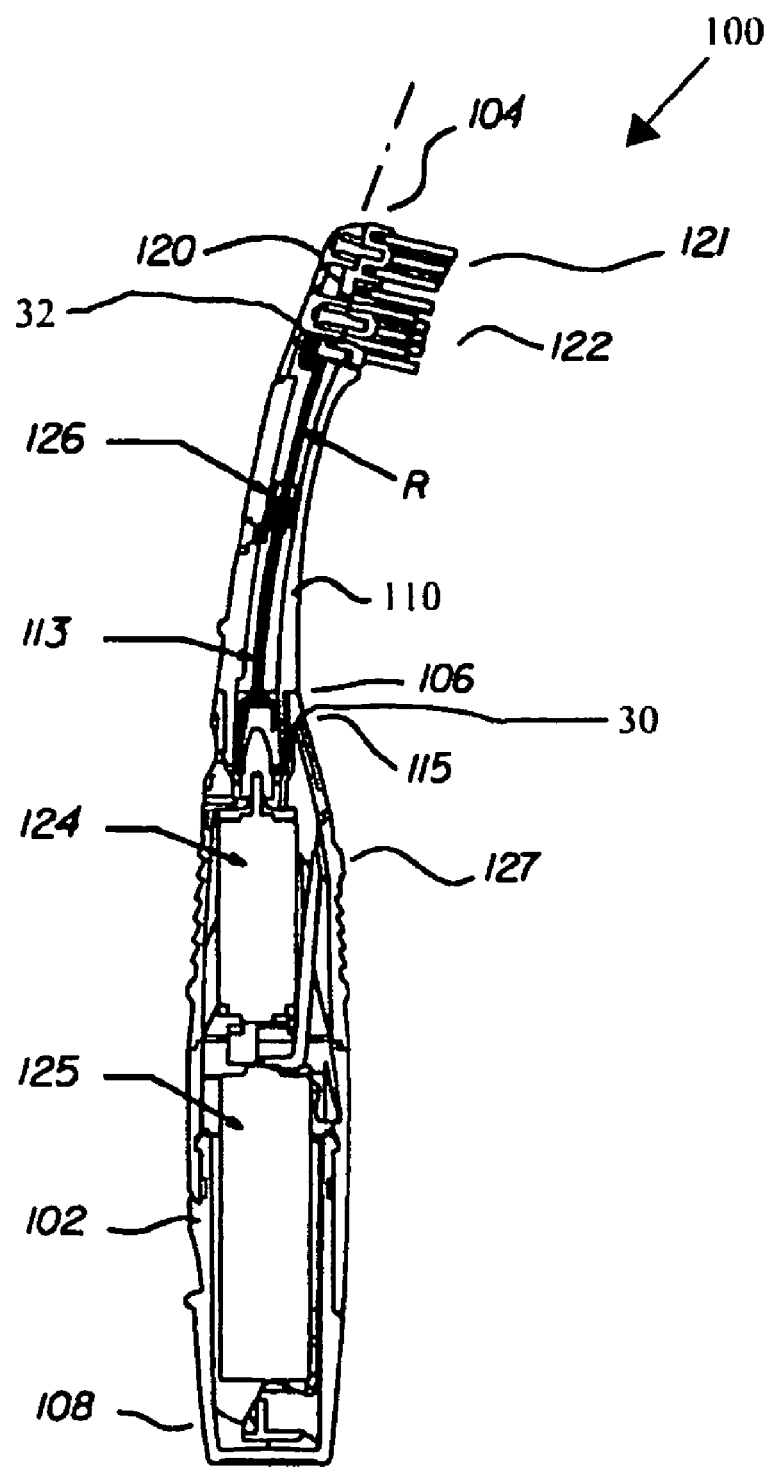
FIG. 1 is a side elevational view of a preferred embodiment of a powered toothbrush in accordance with the teachings of the present invention.
Figure 2:
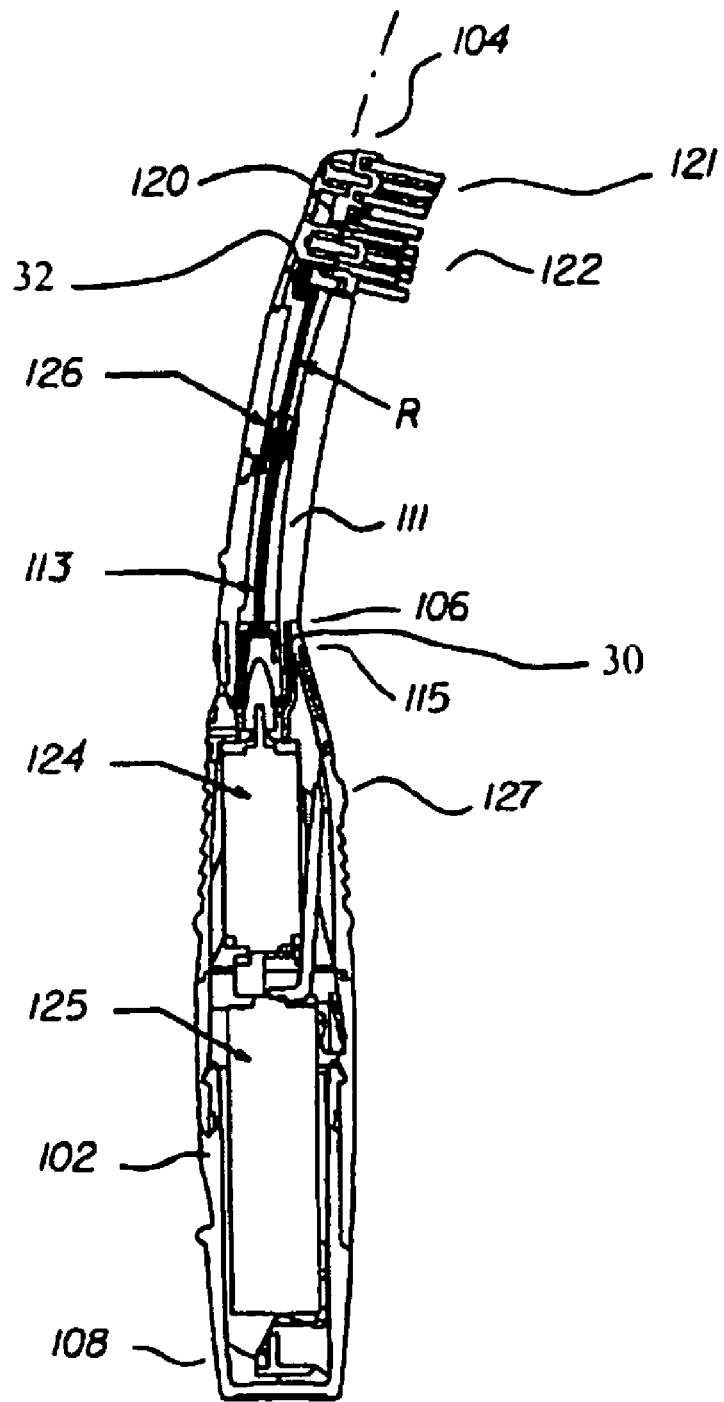
FIG. 2 is a side elevational view of a powered toothbrush having a curved tubular neck portion with a constant radius in accordance with an alternative embodiment of the invention.

Referring now to the drawing, a preferred embodiment of a powered toothbrush in accordance with the teachings of the present invention is shown in FIG. 1. As is shown in FIG. 1, the powered toothbrush 100 includes a handle portion 102 at a proximal end thereof that defines an interior compartment for housing various toothbrush components, and a brush section 104 that is defined by a neck portion 110 that terminates in a head 120 at a distal end of toothbrush 100. The handle portion 102 has a free proximal base support end member 108. The neck portion 110 is the portion of the powered toothbrush 100 that extends between handle 102 and head 120. The neck portion 110 also defines an interior compartment 111 for housing various components of the toothbrush, such as curved flexible shaft 113. Preferably, powered toothbrush 100 is water-repellant.

The neck portion 110 and the handle portion 102 can be constructed as a unitary member by forming neck portion 110 integral to handle portion 102 at neck end 106 of the handle portion 102, or can be formed detachable from handle portion 102 at neck end 106 of neck portion 110. A first interface 30 is formed at the neck end 106 by contact between neck portion 110 and the handle portion 102. In accordance with this detachable embodiment, combined neck portion 110 and head 104 can be removed from the handle portion 102 to permit cleaning, servicing and/or interchanging of either handle 102 or the combined neck 110 and head 120 (brush section 104). When the neck portion 120 is formed to be detachable from handle 102, neck end 106 preferably includes a connector linkage 115 that is adapted to be detachably joined to handle portion 102 using traditional techniques. It will be appreciated that the point of attachment may be between the head portion 120 and the neck portion 110 such that the head 120 is of a refill type head. As a result, a second interface 32 is formed by contact between neck portion 110 and the head 120. Furthermore, the head 120 is formed of a first bristle carrier 121 which rotates in a first rotational direction. The head 120 also includes a second bristle carrier 122 which can either include stationary bristles, or rotate in the same direction as first bristle carrier 121, or in an opposite direction therefrom.

Polymeric materials, such as plastics, or other suitable materials may be used to fabricate the neck, handle and flexible drive shaft. Preferably, thermoplastic elastomers may be used to fabricate the flexible drive shaft.

In a preferred embodiment, the curved neck is of a constant curvature with a radius R, as seen in FIG. 1. R is from about 150 mm to about 450 mm. Preferably, R is 250 mm.

The powered toothbrush 100 includes a drive mechanism to effectuate certain movement of certain parts of the toothbrush, and more specifically for causing movement of the movable bristle carrier 121, and bristle carrier 122, if movable via flexible drive shaft 113. One exemplary drive mechanism is disclosed in U.S. Pat. No. 5,625,916 to McDougall, which is incorporated herein by reference.

The drive mechanism for powered toothbrush 100 can be any type of drive, e.g., a rotating drive, an oscillating drive, an eccentric drive, an unbalanced-generated drive, a drive having one or more gearing mechanisms, and/or the like, that is capable of performing the intended function. The drive mechanism can be realized in the form of an electric motor or other type of motor and the movement generated by the drive can be imparted to one or more sections of the head or to other elements which can be present at the brush section, such as bristle tufts and elastomeric members. When the toothbrush 100 includes an oscillating drive mechanism, for example, the interior compartment of a handle 102 houses the motor 124 operatively connected to the drive shaft and a source to power the motor, such as battery 125.

If desired for overload protection, a conventionally designed, spring-loaded, slipping clutch may be included at any convenient location. A clutch is any of the various number of devices for engaging and disengaging two working parts of a shaft or of a shaft and a driving mechanism. As it relates to powered toothbrush, the integration of a clutching mechanism, for example, avoids stalling of the motor when excessive force is applied to the brush carrier(s).

In a preferred embodiment, clutch 126 connects flexible drive shaft 113 to motor 124. Clutch 126 is adapted to disengage flexible drive shaft 113 from motor 124 upon overpressure, thereby preventing or minimizing damage to, for example, bristle carriers 121 and 122.

When the drive mechanism is actuated and the flexible drive shaft is rotated, the movement of a crank end thereof imparts an oscillating back and forth movement of bristle carrier 121, and optionally, bristle carrier 122, through an angle between about 10° to about 60°. In a preferred exemplary embodiment, the movement is through an angle of between 10° to about 30°.

In order to simplify user interface, the powered toothbrush of this invention includes on/off switch 127 for activating/deactivating the motor. Preferably, on/off switch 127 is provided along a face of the handle portion in a thumb depression.

Although the invention has been particularly shown and described with reference to certain preferred embodiments, it will be readily appreciated by those of ordinary skill in the art that various changes and modifications may be made therein without departing from the spirit and scope of the invention. It is intended that the claims be interpreted as including the foregoing as well as any such changes and modifications.

What is claimed is:

1. A powered toothbrush comprising:
   a handle having an inner cavity formed therein and a base member at a first end thereof;
   a rotary drive member disposed within said inner cavity;
   a curved tubular neck portion detachably coupled to and extending from a second end of said handle so that a first interface is formed by contact between the neck portion and the handle, a radial axis extending along the curved tubular neck portion;

a head detachably coupled to the neck portion so that a second interface is formed by contact between the neck portion and the head, the head including at least first and second bristle carriers comprising bristles, wherein the first bristle carrier is adapted to move in a first rotational direction and the second bristle carrier is adapted to move in a second rotational direction, the first and second bristle carriers being disposed along said radial axis;

the neck portion curved at a constant radius of curvature from the first interface to the second interface;

a curved flexible drive shaft for moving the at least one bristle carrier in the first rotational direction and the other bristle carrier in the second rotational direction, the flexible drive shaft rotatably disposed within said curved tubular neck portion, the flexible drive shaft having a first end point and a second end point, the first end point thereof being drivably connected to said drive member through a connector linkage, the first end point of the flexible shaft located at the first interface, and the second end point thereof being operably connected to the first and second bristle carriers, the second end point of the flexible shaft located at the second interface, said flexible drive shaft being rotationally responsive to said rotary drive member, and wherein said flexible drive shaft comprises a thermoplastic elastomer; and a clutch positioned along the flexible drive shaft to disengage the flexible drive shaft from the rotary drive member upon overpressure to prevent or minimize damage to the first and second carriers.

2. The powered toothbrush according to claim 1, wherein said first rotational direction and the second rotational direction are the same.

3. The powered toothbrush according to claim 1, wherein said handle comprises a polymeric material.

4. The powered toothbrush according to claim 1, wherein one of the first and second bristle carriers includes at least one elastomeric cleaning member extending therefrom.

5. The powered toothbrush according to claim 1, wherein the neck portion includes a connector to detachably couple the neck portion to the handle, the connector having a distal end including an inclined protrusion, the inner cavity of the handle having a depression for receiving the inclined protrusion for detachably joining to the handle.

6. The powered toothbrush according to claim 1, wherein said first rotational direction comprise oscillation movement between 30 degrees to 60 degrees.

7. The powered toothbrush according to claim 6, wherein the second end of the flexible drive shaft includes a recess portion for receiving a portion of the rotary drive member therein.

8. The powered toothbrush of claim 1 wherein the neck portion, the handle and the head are non-unitary with respect to each other.

9. The powered toothbrush of claim 1 wherein the first end point of the flexible drive shaft is formed by a coupling having a recess and the second end point of the flexible drive shaft is formed by an L-shaped portion, and wherein the flexible drive shaft is substantially curved along the entirety of its length from the coupling to the L-shaped portion.

10. A powered toothbrush comprising:

a handle having an inner cavity formed therein and a base member at one end thereof;

a rotary drive member disposed within said inner cavity;

a curved tubular neck having a constant radius of curvature extending from another end of said handle opposite said one end;

wherein the neck includes a connector to detachably join the handle so that a first interface is formed by contact between the neck portion and the handle, the connector having a distal end including an inclined protrusion, the inner cavity of the handle having a depression for receiving the inclined protrusion for detachably joining the handle;

a head detachably coupled to the curved tubular neck so that a second interface is formed by contact between the neck portion and the head, the head including at least one carrier comprising tooth cleaning elements, wherein the at least one carrier is adapted to move in a first rotational direction;

a flexible drive shaft rotatably disposed within and extending generally parallel to the curved tubular neck;

the flexible drive shaft for moving the at least one carrier in a first rotational direction, the flexible drive shaft having a first end and a second end, the first end of the flexible drive shaft drivably connected to said drive member through a connector linkage, the second end operatively connected to the carrier within the head, said flexible drive shaft being rotationally responsive to said rotary drive member to rotate the carrier;

wherein the first end of the flexible drive shaft is located at the first interface and the second end of the flexible drive shaft is located at the second interface; and a clutch positioned along the flexible drive shaft to disengage the flexible drive shaft from the rotary drive member upon overpressure to prevent or minimize damage to the at least one carrier.

11. The powered toothbrush according to claim 10, wherein said powered toothbrush comprises at least two carriers in which one of the carriers is stationary during rotational movement of the flexible drive shaft.

12. The powered toothbrush according to claim 10, wherein said handle comprises a polymeric material.

13. The powered toothbrush according to claim 10, wherein the tooth cleaning elements include at least one elastomeric cleaning element.

14. The powered toothbrush according to claim 13, wherein the tooth cleaning elements include bristles.

15. The powered toothbrush according to claim 13, wherein said flexible drive shaft comprises a thermoplastic elastomer.

16. The powered toothbrush according to claim 10, wherein said first rotational direction ranges between 30 degrees to 60 degrees.

17. The powered toothbrush according to claim 10, wherein the first end of the flexible drive shaft is disposed within the curved tubular neck.

18. The powered toothbrush according to claim 10, wherein the constant radius is provided from about 150 mm to 450 mm.

19. The powered toothbrush according to claim 10, wherein the at least one carrier comprises two movable carriers including tooth cleaning elements, the two carriers being disposed along the constant radius.

20. The powered toothbrush according to claim 10, wherein the at least one carrier comprises two movable carriers including tooth cleaning elements, and the two carriers rotate in the first rotational direction responsive to rotational movement of the flexible drive shaft.

* * * * *